(12) United States Patent
Khazaka

(10) Patent No.: US 6,251,070 B1
(45) Date of Patent: Jun. 26, 2001

(54) DEVICE AND A METHOD FOR MEASURING SKIN PARAMETERS

(75) Inventor: Gabriel Khazaka, Cologne (DE)

(73) Assignee: Courage + Khazaka electronic GmbH, Cologne (DE)

( * ) Notice: Subject to any disclaimer, the term of this patent is extended or adjusted under 35 U.S.C. 154(b) by 0 days.

(21) Appl. No.: 09/406,856

(22) Filed: Sep. 29, 1999

(30) Foreign Application Priority Data

Sep. 30, 1998 (EP) .................................................. 98118533

(51) Int. Cl.⁷ ....................................................... A61B 5/00
(52) U.S. Cl. .......................... 600/306; 600/310; 600/573; 600/584
(58) Field of Search .................................... 600/300, 306, 600/309–310, 345, 362–363, 573, 584; 604/20, 290

(56) References Cited

U.S. PATENT DOCUMENTS

| | | |
|---|---|---|
| 4,224,950 | 9/1980 | Bore et al. . |
| 5,722,397 | * 3/1998 | Eppstein ............................ 600/310 X |
| 5,750,356 | * 5/1998 | Spack et al. ........................ 435/7.24 |

FOREIGN PATENT DOCUMENTS

| | | |
|---|---|---|
| 0312736 | 8/1988 | (EP) . |
| 0129598 | 12/1988 | (EP) . |
| 0783867 | 11/1996 | (EP) . |

\* cited by examiner

Primary Examiner—John P. Lacyk
Assistant Examiner—Ryan Carter
(74) Attorney, Agent, or Firm—Diller, Ramik & Wight

(57) ABSTRACT

A device for measuring parameters of the skin of living beings on the surface of the skin to be examined, comprising a housing with a light source, an optical recording means, and an image processing means, wherein the housing consists of an applicator, in which an optical recording means formed by a video camera and a light emitting means connected to a light source are integrated, the applicator, which is adapted to be placed on the skin surface, holding the video camera and the light emitting means at a predetermined distance from the skin surface.

19 Claims, 1 Drawing Sheet

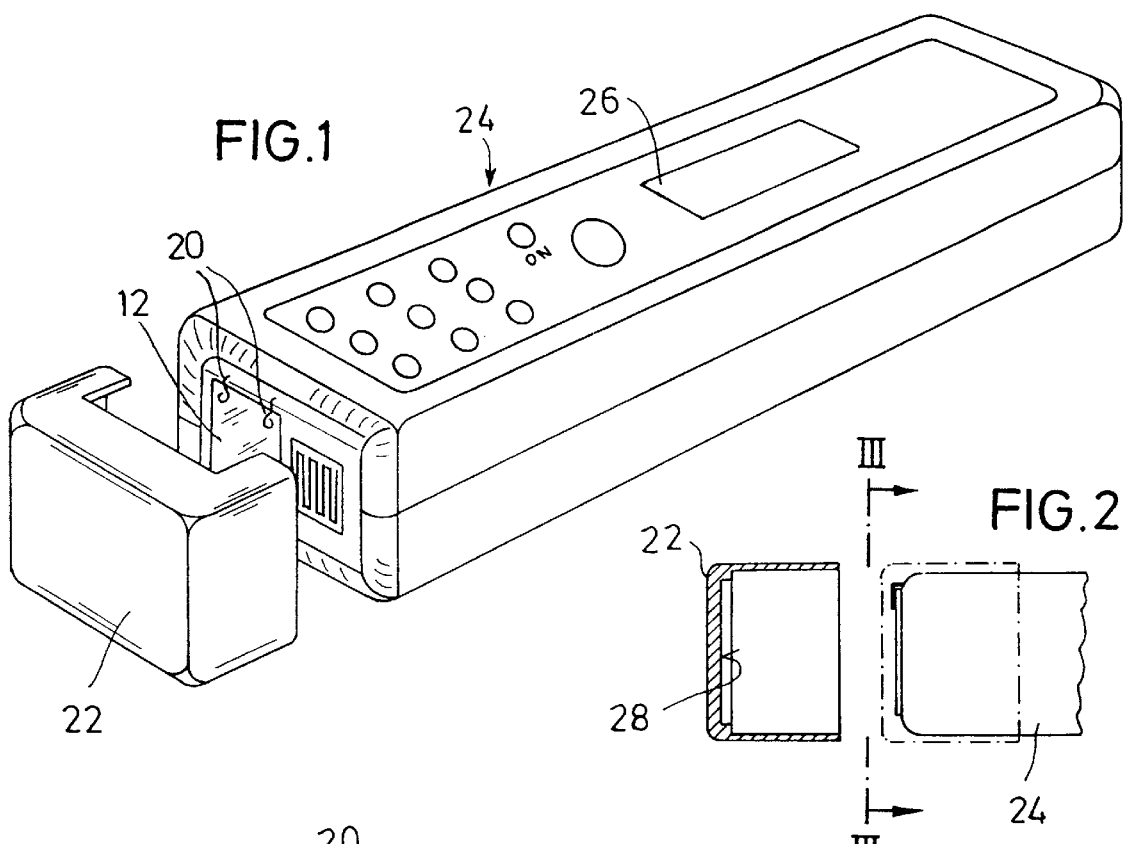
FIG.1
FIG.2
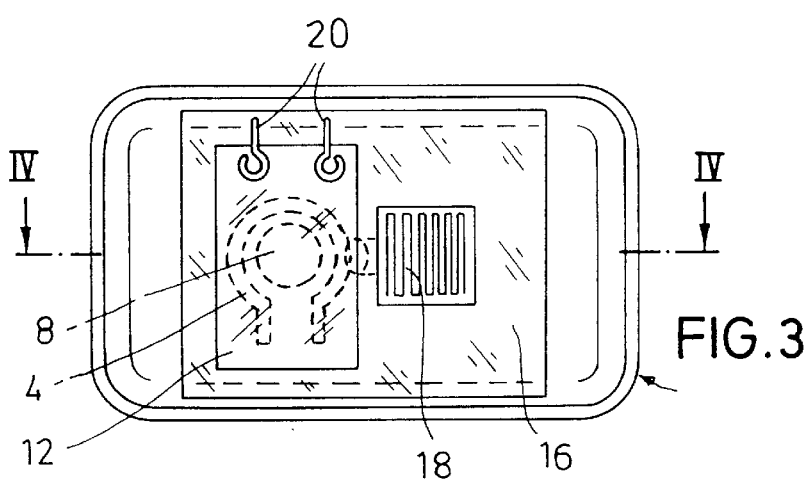
FIG.3
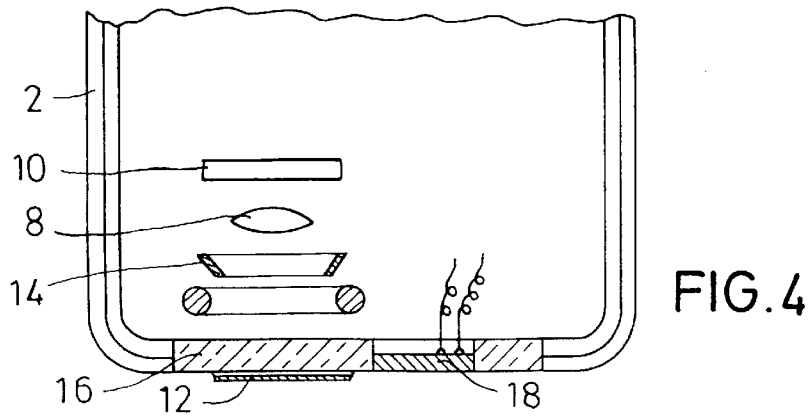
FIG.4

DEVICE AND A METHOD FOR MEASURING SKIN PARAMETERS

BACKGROUND OF THE INVENTION

The present invention refers to a device and a method for measuring skin parameters.

Dermographic apparatus are known that are used to measure the topography of the skin, e.g. regarding scaling or wrinkles, with which predetermined skin parameters may be measured.

It is known, for example, to document changes of the skin using a photographic camera with macro optics.

Further, microscopic and macroscopic video cameras are known that are connected to image processing means for storing and reproducing, as well as measuring and analyzing the images.

It is a disadvantage of the known devices for measuring the skin surface that they provide no images of sufficient contrast so that evaluating the images is difficult.

It is an object of the present invention to develop a device of the above mentioned kind such that a better contrast is achieved by an improved surface reflection.

SUMMARY OF THE INVENTION

Advantageously, the housing of the present invention consists of an applicator in which an optical recording means, a video camera in this instance, and a light emitting means connected to a light source are integrated, the applicator, which is adapted to be placed on the skin surface, holds the video camera and the light emitting means at a predetermined distance from the skin surface.

Arranging the light emitting means within the applicator adapted to be set onto the skin surface allows for recordings of the skin surface that are rich in contrast, the light source either being external and connected with the light emitting means via light guides or it is integrated internally in the applicator.

The use of a neon light tube as the light source makes it possible to use a shorter wavelength, as compared to visible light, which results in a higher contrast.

Preferably, the light emitting means is arranged annularly around the optics of the video camera. Thus, the skin surface is illuminated uniformly and without shadows.

The video signal from the video camera may be transmitted to the image processing means by radio signals. In this case, the applicator with the video camera is freely movable and not dependent on a cable.

The light source for measuring the topography of the skin emits light in a wavelength range between about 350 to 400 nm, the CCD chip of the video camera being more sensitive to that wavelength range than to visible light. The shorter wavelength, as compared to visible light, allows for a surface reflection much richer in contrast with which video pictures with a significantly higher contrast may be obtained.

It is another advantage that, for example, dead skin scales are caused to emit fluorescent light, whereby they can be distinguished from other skin portions on the video picture.

Another feature of the present device is that for measuring secretions from the skin, a replaceable film is provided at a distance from the optics, the initially opaque film absorbing the secretions and becoming transparent as it absorbs them. Such a device allows for a dynamic measuring of the rate at which the secretions of the skin are produced, the absorption in the foil being documented over time by the video camera.

To measure the secretion of sebum from the skin, a sebum absorbing, initially opaque film that becomes transparent with the absorption of sebum, whereas the secretion of humidity from the skin a humidity absorbing, initially opaque film is used that becomes transparent with the absorption of humidity.

The image processing means comprises an image analyzing means that, using the online video signal or a stored video signal, performs the measuring of the skin parameters, the statistic evaluation and the documentation of the skin parameter data.

BRIEF DESCRIPTION OF THE DRAWINGS

The following is a detailed description of embodiments of the invention with reference to the accompanying drawings.

In the Figures:

FIG. 1—a perspective view of the present applicator with a video camera and a neon light tube integrated in the applicator, FIG. 2—a section through a reflection cap, FIG. 3—a front view of the applicator, and FIG. 4—a partial cross section through the applicator.

DETAILED DESCRIPTION OF THE PREFERRED EMBODIMENTS

An applicator 2 with a housing accommodating a light source consisting of a neon light tube 4, as well as an optical recording means, a video camera 6 in this instance, is illustrated in FIG. 1. The applicator 2 adapted to be set onto the skin keeps the video camera 6 and the neon tube 4 at a predetermined distance from the skin surface. Current is supplied, for example, by a lithium battery or an accumulator also arranged in that applicator 2.

The fixed distance from the surface of the skin makes it possible to use an optical recording means with a fixed focusing. As an alternative, the optics of the video camera may be a variable optics allowing for different factors of magnification.

Preferably, the neon tube 4 is arranged annularly about the optical lenses 8 of the video camera 6.

Instead of the neon tube 4, another light emitting means may be used. When an external light source is employed, the light may be introduced into the applicator 2 via light guides.

Preferably, the applicator has an integrated current supply so that only the video signal must be transferred to an image processing means. Here, it is also possible to transfer the video signal to the image processing means by radio.

Preferably, the neon tube or another light source emits light in a wavelength range between about 350 to 400 nm for measuring the topography of the skin. In this wavelength range, the video camera 6 can picture the skin with an increased contrast range, the CCD chip 10 of the video camera 6 possibly being more sensitive to the above mentioned wavelength range than to visible light. The increase in the contrast range by an improved surface reflection is advantageous in that the analysis and the processing of the picture may be performed with a higher precision and a better reproducibility. It is a further advantage that dead scales are caused to fluoresce, whereby they a particularly discernible when analyzing the image.

The same applicator 2 may also be used to measure the sebum secretion of the skin surface. To this end, a replaceable sebum absorbing, initially opaque film that becomes transparent with the absorption of the sebum is arranged at a distance in front of the optical means, the film being adapted to be placed directly on the skin surface to be examined. The sebum absorbing film 12 consists, for example, of a microporous hydrophobic polypropylene film with a porosity of 20 to 50%, a thickness between 20 and 30 μm and a pore size between 0.03 and 0.15 μm. Such a film has a uniform distribution of micropores and is opaque in the original state. Upon contact with sebum, the pores fill, whereby the film becomes transparent at the corresponding locations. Therefore, such a film is suitable for various examinations regarding the secretion of sebum from the skin, if the film is brought in contact with the skin surface, using a little pressure, if need be. In combination with the video camera 6, the absorption of the sebum by the film may be documented over time. Thus, dynamic sebum measurements may be performed that also for a determination of the rate at which sebum is produced by the skin.

In order to measure the secretion of humidity from the skin surface, a humidity absorbing film is used that becomes transparent with the absorption of humidity.

The applicator thus allows for an immediate examination of the skin surface regarding scaling and wrinkles, including the documentation and the measuring using an image processing means and an image analyzing means. Further, the applicator may be used for quantitative dynamic measurements of skin secretions, in particular for determining the rate at which the skin secretions are produced.

FIG. 3 is a partial cross section of the applicator 2. The neon tube 4 may be arranged in front of the optical lenses 8 or to the side thereof. Between the neon tube 4 and the optical lenses 8 or a set of optical lenses 8, a suitable screen 14, e.g. annular in shape, may be disposed that prevents the neon tube 4 from blinding the CCD chip 10.

The contact surface of the applicator 2 on the skin surface preferably is a transparent pane 16 integrated into the housing 2 and at the same time serving as a spacer so that the video camera may be operated in the fixed focus mode. The surface of the transparent pane 16 may be coated. As illustrated in FIG. 2, the transparent pane 16 also serves to receive the sebum and humidity absorbing film 12.

The film 12 is held on the transparent pane 16 by resilient clamps 20, for example.

It is also possible to clamp a film 12 on the transparent pane 16 that has a sebum absorbing and a humidity absorbing portion so that measures may be taken simultaneously.

As an alternative to a humidity absorbing film, a humidity sensor 18, as shown in FIG. 3, may be provided in the transparent pane 16 with which the humidity of the skin may be measured simultaneously or with a delay in time.

The humidity sensor 18 is integrated into the pane 16 such that the surface of the humidity sensor is flush with the outer surface of the pane 16.

It is another advantage of the applicator 2 that both the analysis of the topography of the skin and the measurement of the skin sebum and the humidity of the skin may be done simultaneously and in a common contact surface formed by the transparent pane 16.

As is evident from FIGS. 1 and 2, a cap 22 may be set onto the applicator 2, whereby in the quantitative measuring of the secretions of the skin surface, the reflection properties of the cap 22 allow for a zero value measurement. The inner side of the cap 22 may have a black or mirrored surface 28.

The image processing means comprises an image analyzing means that performs the measurement of the skin parameters, the statistic evaluation and the documentation of the skin parameter data using the online video signal from the video camera 6 or stored video signals. The image analyzing means may be used in measuring the secretion of skins to evaluate the change of the video signals over time for the determination of the rate at which the surface of the skin produces secretions.

FIG. 1 illustrates a schematic representation of a control panel 24 with which the functions of the applicator 2 may be controlled.

Further, the applicator 2 may be provided with a display panel 26, e.g. for the display of a measured value or a function.

What is claimed is:

1. A device for measuring secretions from skin of living beings on a surface of skin to be examined comprising a housing with a light source, an optical recording means, and an image processing means, the housing including an applicator, in which an optical recording means formed by a video camera and a light emitting means connecting to a light source are integrated, the applicator, which is adapted to be placed on the skin surface, holding the video camera and the light emitting means at a predetermined distance from the skin surface, a replaceable secretion absorbing film that is initially opaque and becomes transparent with the absorption of skin secretions, being arranged at a distance in front of the optical recording means, the film being adapted to set directly on the skin surface to be examined.

2. The device of claim 1, wherein the film is sebum absorbing film that is initially opaque and becomes transparent as it absorbs sebum.

3. The device of claim 1, wherein the film is a humidity absorbing film that is initially opaque and becomes transparent as it absorbs humidity.

4. The device of claim 1, wherein the light source is a neon light tube integrated in the applicator.

5. The device of claim 1, wherein the light source is external and is connected with the light emitting means via light guides.

6. The device of claim 1, wherein the light emitting means is arranged annularly about the optics of the video camera.

7. The device of claim 1, wherein the video signal from the video camera may be transmitted to the image processing means by radio.

8. The device of claim 1 characterized in that, for measuring the topography of the skin, the light source emits light in a wavelength range between about 350 and 400 nm, the CCD chip of the video camera being more sensitive to this wavelength range than to visible light.

9. The device of claim 1, wherein the applicator comprises a pane forming a transparent contact surface for setting the applicator on the skin surface.

10. The device of claim 1, wherein the image processing means stores the variation in time of the absorption of sebum or humidity in the film as video signal.

11. The device of claim 1, wherein a reflection cap is placed on the film to determine a reference measuring value.

12. The device of claim 1, wherein the image processing means comprises an image analyzing means for performing the measuring of skin parameters, statistic evaluation and documentation of skin parameter data using the online video signal of the video camera or the stored video signals.

13. The device of claim 12, wherein the image analyzing means evaluates the variation in time of the video signals to determine the rate at which the skin produces sebum and humidity.

14. The device of claim 1, wherein a current supply means is integrated in the applicator.

15. A method for measuring skin secretions by placing an initially opaque film on a skin surface to be examined, which film absorbs secretions and becomes transparent as it absorbs the secretions, the secretions being measured by recording the variation in time of the absorption by the film using a video camera integrated in the applicator and an integrated light emitting means illuminating the film, and by evaluating the video signals of the video camera to determine the rate at which the skin secretions are produced.

16. The method of claim 15, wherein the secretion of sebum from the skin is measured by a sebum absorbing film that is initially opaque and becomes transparent as it absorbs sebum.

17. The method of claim 15, wherein the secretion of humidity from the skin is measured by a humidity absorbing film that is initially opaque and becomes transparent as it absorbs humidity.

18. The method of claim 15, wherein the film is held at a predetermined distance in front of the video camera and is set immediately on the skin surface to be examined, together with the applicator including the video camera and the integrated light emitting means.

19. The method of claim 15, wherein a reference value is determined by a reflection surface placed on the film.

* * * * *